(12) United States Patent
Taff et al.

(10) Patent No.: US 12,029,475 B2
(45) Date of Patent: Jul. 9, 2024

(54) THROMBECTOMY USING BOTH ELECTROSTATIC AND SUCTION FORCES

(71) Applicant: MAGNETO THROMBECTOMY SOLUTIONS LTD., Or Yehuda (IL)

(72) Inventors: Yuval Taff, Tel Aviv (IL); Gal Stern, Tel Aviv (IL); Itzhak Orion, Beer Sheva (IL)

(73) Assignee: MAGNETO THROMBECTOMY SOLUTIONS LTD., Or Yehuda (IL)

( * ) Notice: Subject to any disclaimer, the term of this patent is extended or adjusted under 35 U.S.C. 154(b) by 1193 days.

(21) Appl. No.: 16/381,014

(22) Filed: Apr. 11, 2019

(65) Prior Publication Data
US 2019/0262069 A1    Aug. 29, 2019

Related U.S. Application Data

(63) Continuation-in-part of application No. PCT/IB2018/051731, filed on Mar. 15, 2018.
(Continued)

(51) Int. Cl.
*A61B 18/14* (2006.01)
*A61B 18/00* (2006.01)
*A61B 17/22* (2006.01)

(52) U.S. Cl.
CPC ............ *A61B 18/1492* (2013.01); *A61B 2017/22067* (2013.01); *A61B 2017/22079* (2013.01);
(Continued)

(58) Field of Classification Search
CPC ........... A61B 2018/0041; A61B 17/22; A61B 2017/22067; A61B 2017/220079
See application file for complete search history.

(56) References Cited

U.S. PATENT DOCUMENTS

| 4,027,674 A | 6/1977 | Tessler et al. |
| 4,682,596 A | 7/1987 | Bales et al. |

(Continued)

FOREIGN PATENT DOCUMENTS

| CN | 103732169 A | 4/2014 |
| CN | 104207844 A | 12/2014 |

(Continued)

OTHER PUBLICATIONS

Australian application # 2018206023 office action dated May 8, 2020.
(Continued)

*Primary Examiner* — Jaymi E Della
*Assistant Examiner* — Abigail M Ziegler
(74) *Attorney, Agent, or Firm* — KLIGLER & ASSOCIATES PATENT ATTORNEYS LTD.

(57) ABSTRACT

Apparatus for removal of a thrombus from a body of a subject includes an electrically-insulating tube, which includes a distal end having a circumferential wall that is shaped to define one or more perforations, configured for insertion into the body of the subject, an outer electrode, disposed over the distal end of the electrically-insulating tube, and configured to lie at least partly within the thrombus while the electrically-insulating tube is inside the body of the subject, and an inner electrode, configured to lie, within the tube, opposite the perforations, while the outer electrode lies at least partly within the thrombus. The outer electrode is configured to attract the thrombus while the outer electrode lies at least partly within the thrombus and the inner electrode lies opposite the perforations, when a positive voltage is applied between the outer electrode and the inner electrode such that electric current flows through the perforations.

21 Claims, 10 Drawing Sheets

Related U.S. Application Data

(60) Provisional application No. 62/713,570, filed on Aug. 2, 2018, provisional application No. 62/474,628, filed on Mar. 22, 2017.

(52) U.S. Cl.
CPC .............. *A61B 2018/00083* (2013.01); *A61B 2018/0041* (2013.01); *A61B 2018/1435* (2013.01); *A61B 2018/144* (2013.01); *A61B 2218/007* (2013.01)

(56) References Cited

U.S. PATENT DOCUMENTS

| | | | |
|---|---|---|---|
| 5,122,136 A | 2/1992 | Guglielmi | |
| 5,125,928 A | 6/1992 | Parins et al. | |
| 5,300,068 A | 4/1994 | Rosar et al. | |
| 5,354,295 A | 10/1994 | Guglielmi et al. | |
| 5,433,708 A * | 7/1995 | Nichols | A61B 18/082 604/113 |
| 5,449,357 A * | 9/1995 | Zinnanti | A61M 1/0062 606/49 |
| 5,507,743 A | 4/1996 | Edwards et al. | |
| 5,545,193 A | 8/1996 | Fleischman et al. | |
| 5,569,204 A | 10/1996 | Cramer | |
| 5,603,731 A | 2/1997 | Whitney | |
| 5,722,401 A | 3/1998 | Pietroski et al. | |
| 5,827,278 A | 10/1998 | Webster | |
| 5,851,206 A | 12/1998 | Guglielmi et al. | |
| 5,876,398 A * | 3/1999 | Mulier | A61B 18/1492 606/41 |
| 5,913,854 A * | 6/1999 | Maguire | A61B 18/1492 606/41 |
| 5,925,042 A | 7/1999 | Gough et al. | |
| 6,047,700 A | 4/2000 | Eggers et al. | |
| 6,179,824 B1 | 1/2001 | Eggers et al. | |
| 6,190,381 B1 | 2/2001 | Olsen et al. | |
| 6,210,404 B1 | 4/2001 | Shadduck | |
| 6,248,113 B1 * | 6/2001 | Fina | A61B 17/22 606/127 |
| 6,322,559 B1 | 11/2001 | Daulton et al. | |
| 6,554,827 B2 | 4/2003 | Chandrasekaran et al. | |
| 6,658,288 B1 | 12/2003 | Hayashi | |
| 6,730,104 B1 | 5/2004 | Sepetka et al. | |
| 6,855,143 B2 | 2/2005 | Davision et al. | |
| 8,197,478 B2 | 6/2012 | Hayashi et al. | |
| 8,473,029 B2 * | 6/2013 | Gerhart | A61B 5/283 600/411 |
| 8,579,893 B2 * | 11/2013 | Hoey | A61B 18/04 606/41 |
| 8,747,416 B2 | 6/2014 | Hakala et al. | |
| 8,814,859 B2 | 8/2014 | Drasler et al. | |
| 8,968,304 B2 | 3/2015 | Katou | |
| 9,795,400 B2 | 10/2017 | Davidson | |
| 10,265,515 B2 | 4/2019 | Davidson | |
| 10,434,295 B2 | 10/2019 | Stigall et al. | |
| 10,499,939 B2 | 12/2019 | Davidson | |
| 10,709,463 B2 | 7/2020 | Girdhar et al. | |
| 10,716,610 B2 | 7/2020 | Yamanishi et al. | |
| 10,758,303 B2 | 9/2020 | Xiao et al. | |
| 10,874,410 B2 | 12/2020 | Scarpine et al. | |
| 10,874,411 B2 | 12/2020 | Nguyen et al. | |
| 10,912,608 B2 | 2/2021 | Lam et al. | |
| 10,987,117 B2 | 4/2021 | Girdhar et al. | |
| 11,058,444 B2 | 7/2021 | Girdhar et al. | |
| 11,090,071 B2 | 8/2021 | Girdhar et al. | |
| 11,160,571 B2 | 11/2021 | Nguyen et al. | |
| 11,191,558 B2 | 12/2021 | Nguyen et al. | |
| 11,317,931 B2 | 5/2022 | Davidson | |
| 11,395,668 B2 | 7/2022 | Girdhar et al. | |
| 11,523,838 B2 | 12/2022 | Nguyen et al. | |
| 11,633,201 B2 | 4/2023 | Girdhar et al. | |
| 11,666,350 B2 | 6/2023 | Nguyen et al. | |
| 2001/0001314 A1 | 5/2001 | Davison et al. | |
| 2002/0058937 A1 | 5/2002 | Maltese et al. | |
| 2002/0072764 A1 | 6/2002 | Sepetka et al. | |
| 2002/0133111 A1 | 9/2002 | Shadduck | |
| 2003/0045870 A1 | 3/2003 | Madsen | |
| 2003/0050634 A1 | 3/2003 | Ellman et al. | |
| 2003/0125787 A1 | 7/2003 | Shcherinsky | |
| 2003/0130571 A1 | 7/2003 | Lattouf | |
| 2004/0073243 A1 | 4/2004 | Sepetka et al. | |
| 2004/0082948 A1 | 4/2004 | Stewart et al. | |
| 2005/0159739 A1 | 7/2005 | Paul et al. | |
| 2005/0251134 A1 | 11/2005 | Woloszko et al. | |
| 2006/0089638 A1 | 4/2006 | Carmel et al. | |
| 2006/0195137 A1 * | 8/2006 | Sepetka | A61B 17/22031 606/200 |
| 2006/0224155 A1 | 10/2006 | Schmaltz | |
| 2007/0027448 A1 * | 2/2007 | Paul | A61B 18/1492 606/41 |
| 2007/0078457 A1 * | 4/2007 | Paul | A61B 18/1492 606/50 |
| 2007/0156082 A1 | 7/2007 | Scherman | |
| 2007/0156130 A1 * | 7/2007 | Thistle | A61B 18/1477 606/41 |
| 2007/0255270 A1 | 11/2007 | Carney | |
| 2008/0161796 A1 | 7/2008 | Cao et al. | |
| 2008/0161803 A1 | 7/2008 | Oral et al. | |
| 2008/0161893 A1 | 7/2008 | Paul et al. | |
| 2008/0262489 A1 | 10/2008 | Steinke | |
| 2009/0248012 A1 | 10/2009 | Maor et al. | |
| 2010/0114017 A1 | 5/2010 | Lenker et al. | |
| 2010/0312223 A1 | 12/2010 | Kozak et al. | |
| 2011/0022045 A1 * | 1/2011 | Cao | A61B 18/1492 606/41 |
| 2011/0144639 A1 | 6/2011 | Govari | |
| 2011/0218528 A1 | 9/2011 | Ogata et al. | |
| 2011/0257649 A1 | 10/2011 | Geistert et al. | |
| 2011/0288541 A1 | 11/2011 | Faure | |
| 2011/0301594 A1 | 12/2011 | Orion | |
| 2011/0308527 A1 | 12/2011 | Harrington et al. | |
| 2012/0130169 A1 | 5/2012 | Mesallum | |
| 2012/0232374 A1 * | 9/2012 | Werneth | A61B 18/1492 600/393 |
| 2012/0239022 A1 * | 9/2012 | Wolfe | A61M 25/0082 606/33 |
| 2012/0296262 A1 | 11/2012 | Ogata et al. | |
| 2013/0090644 A1 * | 4/2013 | Williams | A61B 18/042 606/40 |
| 2013/0123872 A1 | 5/2013 | Bornzin et al. | |
| 2013/0325003 A1 * | 12/2013 | Kapur | A61B 17/22012 606/46 |
| 2014/0074113 A1 * | 3/2014 | Hakala | A61B 17/22 606/128 |
| 2014/0276748 A1 | 9/2014 | Ku et al. | |
| 2014/0276913 A1 | 9/2014 | Tah et al. | |
| 2014/0277013 A1 | 9/2014 | Sepetka et al. | |
| 2014/0309579 A1 | 10/2014 | Rubinsky et al. | |
| 2014/0364896 A1 | 12/2014 | Consigny | |
| 2015/0005792 A1 | 1/2015 | Ahn | |
| 2015/0038963 A1 * | 2/2015 | Panos | A61B 18/1492 606/41 |
| 2015/0133990 A1 | 5/2015 | Davidson | |
| 2016/0066989 A1 | 3/2016 | Davies et al. | |
| 2017/0014272 A1 | 1/2017 | Ray et al. | |
| 2017/0172648 A1 | 6/2017 | Germain et al. | |
| 2017/0348049 A1 | 12/2017 | Vrba et al. | |
| 2018/0116717 A1 | 5/2018 | Taff et al. | |
| 2018/0161085 A1 | 6/2018 | Shin et al. | |
| 2019/0388112 A1 | 12/2019 | Nguyen et al. | |
| 2021/0267612 A1 | 9/2021 | Girdhar et al. | |
| 2022/0022900 A1 | 1/2022 | Nguyen et al. | |
| 2022/0125455 A1 | 4/2022 | Girdhar et al. | |
| 2022/0218372 A1 | 7/2022 | Nguyen et al. | |
| 2022/0218373 A1 | 7/2022 | Davidson | |
| 2022/0387051 A1 | 12/2022 | Girdhar et al. | |

(56) References Cited

U.S. PATENT DOCUMENTS

2023/0064470 A1   3/2023   Girdhar et al.
2023/0113257 A1   7/2023   Nguyen et al.

FOREIGN PATENT DOCUMENTS

| CN | 104224318 A | 12/2014 | | |
|---|---|---|---|---|
| DE | 102010014778 A1 | 10/2011 | | |
| EP | 1602338 A2 | 12/2005 | | |
| EP | 1980200 A2 | 10/2008 | | |
| EP | 2359764 A1 | 8/2011 | | |
| JP | H0663060 A | 3/1994 | | |
| JP | H1057392 A | 3/1998 | | |
| WO | 9426228 A1 | 11/1994 | | |
| WO | 9724993 A1 | 7/1997 | | |
| WO | 0062851 A1 | 10/2000 | | |
| WO | 0124720 A1 | 4/2001 | | |
| WO | 2014025397 A1 | 2/2014 | | |
| WO | 2014151123 A1 | 9/2014 | | |
| WO | WO-2015074032 A1 | * | 5/2015 | ............ A61B 8/445 |
| WO | WO-2015076864 A1 | * | 5/2015 | ......... A61B 18/1492 |
| WO | 2018172891 A1 | 9/2018 | | |
| WO | 2019243992 A1 | 12/2019 | | |

OTHER PUBLICATIONS

European Application # 18736539.0 search report dated Jul. 3, 2020.
European Application # 18772459.6 search report dated Jul. 10, 2020.
International Application # PCT/IB2020/051418 search report dated May 31, 2020.
International Application PCT/IB2019/055032 Search Report dated Oct. 28, 2019.
U.S. Appl. No. 15/859,776 Office Action dated May 19, 2021.
CN Application # 2018800054493 Office Action dated Jun. 2, 2021.
U.S. Appl. No. 15/859,776 Office Action dated Jul. 27, 2021.
EP Application # 18880491.8 Search Report dated Jun. 23, 2021.
Sawyer et al., "Electrical Hemostasis in Uncontrollable Bleeding States", Annais of Surgery, vol. 154, Issue 4, pp. 556-562, Oct. 1961.
Gralla et al., "A dedicated animal model for mechanical thrombectomy in acute stroke", American Journal of Neuroradiology, vol. 27, Issue 6, pp. 1357-1361, Jun.-Jul. 2006.
International Application PCT/IB2018/051731 Search Report dated Jul. 5, 2018.
U.S. Appl. No. 15/859,776 Office Action dated Jan. 29, 2021.
U.S. Appl. No. 15/859,776 Office Action dated Oct. 18, 2021.
JP Application # 2019546193 Office Action dated Oct. 26, 2021.
JP Application # 2019531818 Office Action dated Nov. 2, 2021.
CN Application # 2018800054493 Office Action dated Nov. 9, 2021.
International Application # PCT/IB2021058330 Search Report dated Jan. 12, 2022.
CN Application # 201880017216.5 Office Action dated Dec. 9, 2021.
EP Application # 18880491.8 Office Action dated Feb. 10, 2022.
EP Application # 19823746.3 Search Report dated Mar. 4, 2022.
CN Application # 2018800172165 Office Action dated Apr. 24, 2022.
JP Application # 2022002663 Office Action dated Mar. 7, 2023.
U.S. Appl. No. 17/052,813 Office Action dated Jan. 11, 2024.
EP Application # 18772459.6 Office Action dated Dec. 13, 2023.
EP Application # 18736539.0 Office Action dated Dec. 14, 2023.
CA Application # 3055267 Office Action dated Oct. 23, 2023.
U.S. Appl. No. 17/418,863 Office Action dated Feb. 29, 2024.

* cited by examiner

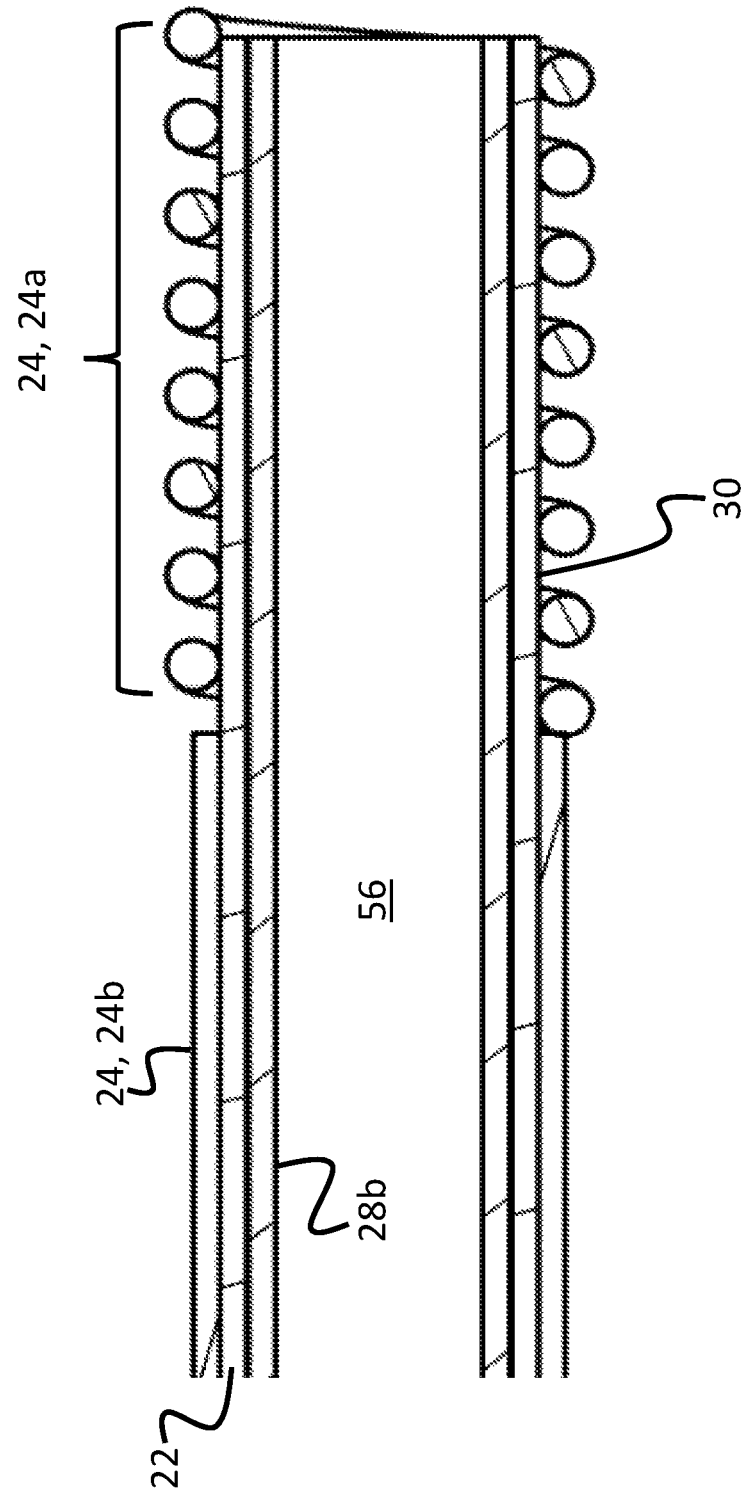

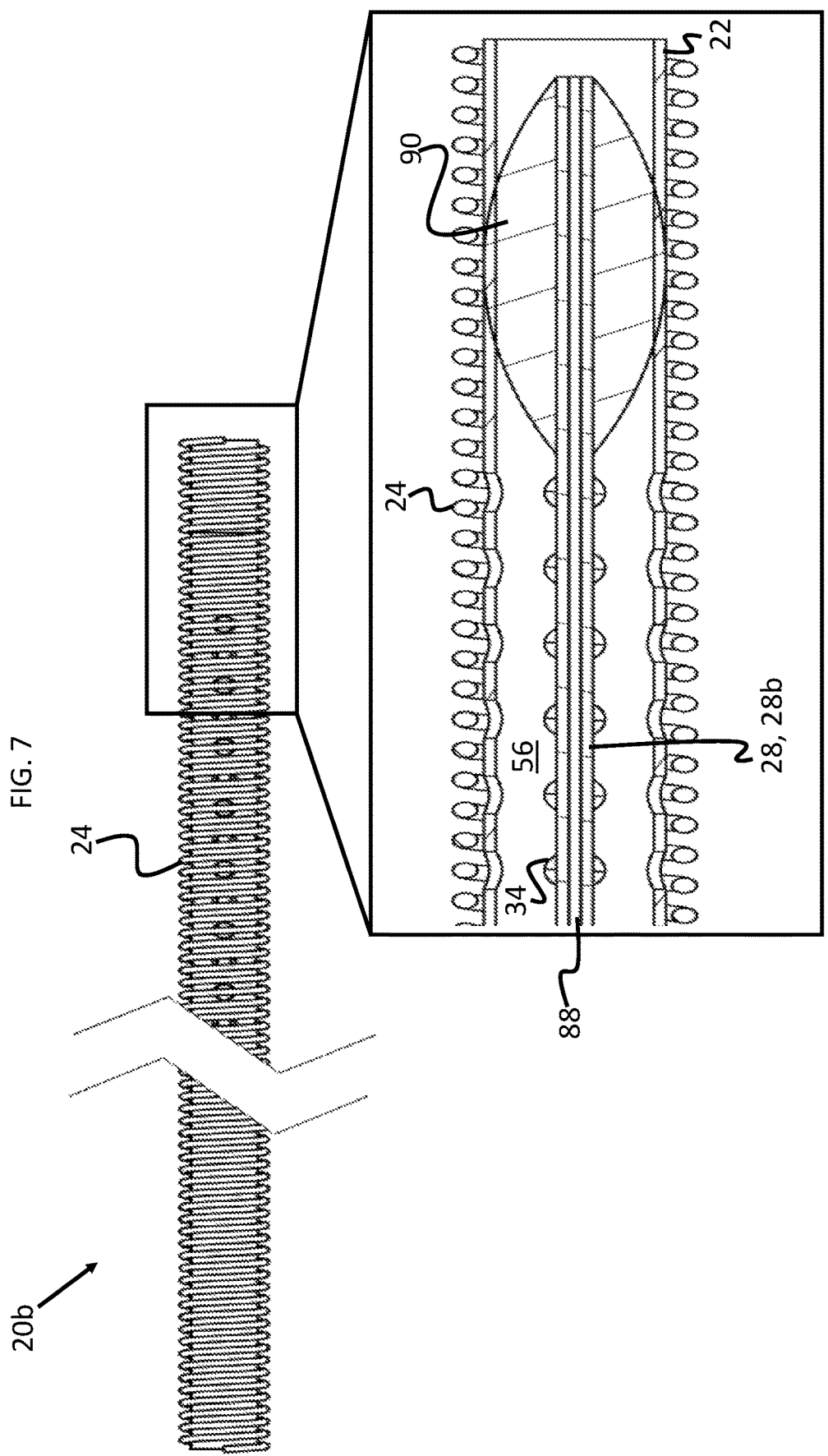

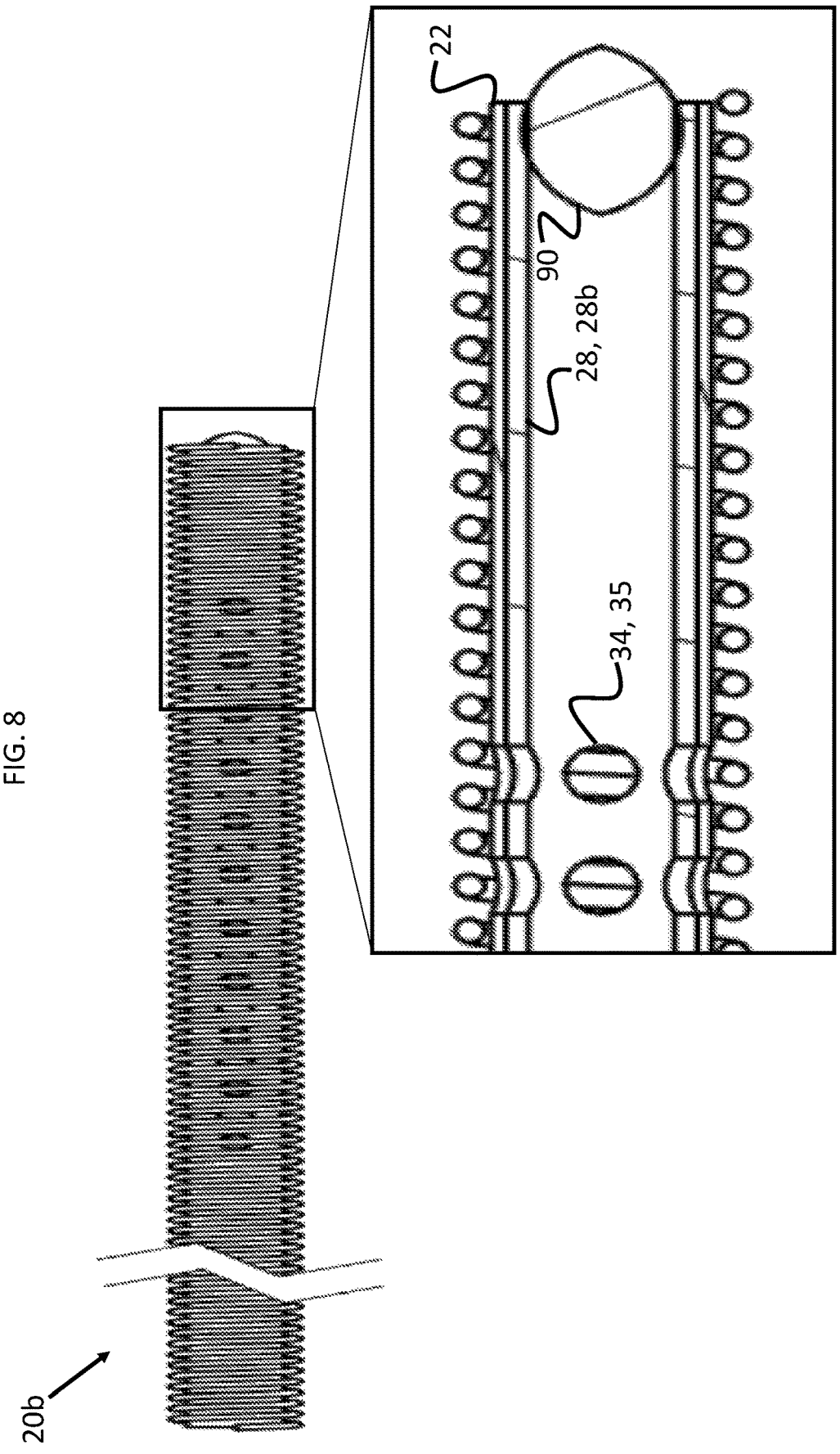

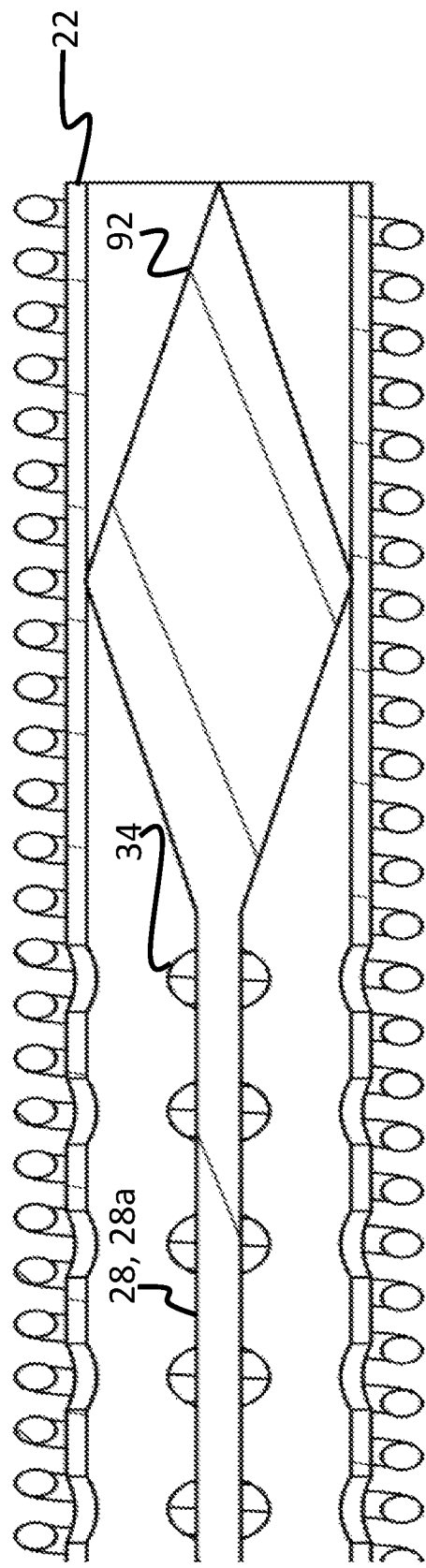

THROMBECTOMY USING BOTH ELECTROSTATIC AND SUCTION FORCES

CROSS-REFERENCE TO RELATED APPLICATIONS

The present application is a continuation-in-part of, and claims the benefit of, International Patent Application PCT/IB2018/051731, entitled "Thrombectomy using both electrostatic and suction forces," filed Mar. 15, 2018, whose disclosure is incorporated herein by reference, which claims the benefit of U.S. Provisional Application 62/474,628, entitled "Radial aspiration thrombectomy device," filed Mar. 22, 2017, whose disclosure is incorporated herein by reference. The present application also claims the benefit of U.S. Provisional Application 62/713,570, entitled "Thrombectomy using both electrostatic and suction forces," filed Aug. 2, 2018, whose disclosure is incorporated herein by reference.

FIELD OF THE INVENTION

Embodiments of the present invention relate to the treatment of thrombi in the body of a subject.

BACKGROUND

US Patent Application Publication 2011/0301594, whose disclosure is incorporated herein by reference, describes a flexible catheter device capable of being introduced into body passages, and withdrawing fluids therefrom or introducing fluids thereinto. The device includes electrodes configured to apply electrical voltage signals in the body passage for carrying out thrombus dissolution and/or thrombectomy, wherein one of said electrodes is designed to contact the thrombus material and remove it or dissolve it, and wherein the electrical voltage signals include a unipolar pulsatile voltage signal.

US Patent Application Publication 2001/0001314 describes electrosurgical apparatus and methods for maintaining patency in body passages subject to occlusion by invasive tissue growth. The apparatus includes an electrode support disposed at a shaft distal end having at least one active electrode arranged thereon, and at least one return electrode proximal to the at least one active electrode. In one embodiment, a plurality of active electrodes each comprising a curved wire loop portion are sealed within a distal portion of the electrode support.

US Patent Application Publication 2004/0073243 describes devices and methods for removing an obstruction from a blood vessel. The devices are deployed in a collapsed condition and are then expanded within the body. The devices are then manipulated to engage and remove the obstruction.

SUMMARY OF THE INVENTION

There is provided, in accordance with some embodiments of the present invention, an apparatus for removal of a thrombus from a body of a subject. The apparatus includes an electrically-insulating tube, which includes a distal end having a circumferential wall that is shaped to define one or more perforations, configured for insertion into the body of the subject. The apparatus further includes an outer electrode, disposed over the distal end of the electrically-insulating tube, and configured to lie at least partly within the thrombus while the electrically-insulating tube is inside the body of the subject. The apparatus further includes an inner electrode, configured to lie, within the tube, opposite the perforations, while the outer electrode lies at least partly within the thrombus. The outer electrode is configured to attract the thrombus while the outer electrode lies at least partly within the thrombus and the inner electrode lies opposite the perforations, when a positive voltage is applied between the outer electrode and the inner electrode such that electric current flows through the perforations.

In some embodiments, the distal end of the electrically-insulating tube is shaped to define a distal opening.

In some embodiments, the apparatus further includes an inflatable balloon, configured to seal the distal opening when inflated at the distal end of the electrically-insulating tube.

In some embodiments,
 the distal end of the electrically-insulating tube is a first distal end,
 the inner electrode includes an electrically-conducting tube including a second distal end, and
 the balloon is coupled to the second distal end.

In some embodiments, the balloon is coupled to an inner wall of the electrically-insulating tube at the distal end of the electrically-insulating tube.

In some embodiments, the inner electrode includes a wire including an enlarged distal head configured to seal the distal opening.

In some embodiments, the distal end of the electrically-insulating tube is closed.

In some embodiments, the distal end of the electrically-insulating tube tapers distally to the perforations.

In some embodiments, the apparatus further includes a pump, configured to facilitate the removal of the thrombus by applying suction to the thrombus, via the perforations, while the voltage is applied.

In some embodiments, the outer electrode includes a coil that wraps around the distal end of the electrically-insulating tube.

In some embodiments, the coil wraps around the distal end of the electrically-insulating tube between the perforations.

In some embodiments, the perforations are first perforations, and the outer electrode includes an electrically-conducting tube shaped to define one or more second perforations that are aligned with the first perforations.

In some embodiments, the perforations are arranged in one or more rows.

In some embodiments, the rows of perforations are distributed circumferentially along the circumferential wall.

In some embodiments, for each of the rows, at least one of the perforations in the row is larger than other perforations in the row.

In some embodiments, at least a proximalmost one of the perforations in the row is larger than the other perforations in the row.

In some embodiments, the inner electrode includes a wire.

In some embodiments, the inner electrode includes an electrically-conducting coil.

In some embodiments, the inner electrode includes an electrically-conducting mesh.

In some embodiments, the inner electrode includes an electrically-conducting tube.

In some embodiments, the perforations are first perforations, and the electrically-conducting tube is shaped to define one or more second perforations that are aligned with the first perforations.

There is further provided, in accordance with some embodiments of the present invention, an apparatus for removal of a thrombus from a body of a subject. The apparatus includes an electrically-insulating tube, which includes a distal end shaped to define a distal opening, configured for insertion into the body of the subject. The apparatus further includes an outer electrode, disposed over the distal end of the electrically-insulating tube, and configured to lie at least partly within the thrombus while the electrically-insulating tube is inside the body of the subject. The apparatus further includes an inner electrode, configured to lie at least partly within the distal end of the electrically-insulating tube while the outer electrode lies at least partly within the thrombus. The outer electrode is configured to attract the thrombus while the outer electrode lies at least partly within the thrombus and the inner electrode lies at least partly within the distal end of the electrically-insulating tube, when a positive voltage is applied between the outer electrode and the inner electrode.

In some embodiments, the apparatus further includes a pump, configured to facilitate the removal of the thrombus by aspirating any detached portions of the thrombus through the distal opening.

In some embodiments, the outer electrode includes a coil that wraps around the distal end of the electrically-insulating tube.

In some embodiments, the outer electrode includes an electrically-conducting tube.

In some embodiments, the inner electrode includes a wire.

In some embodiments, the inner electrode includes an electrically-conducting tube.

In some embodiments, the inner electrode includes an electrically-conducting coil.

In some embodiments, the inner electrode includes an electrically-conducting mesh.

There is further provided, in accordance with some embodiments of the present invention, a method for removing a thrombus from a body of a subject. The method includes inserting an electrically-insulating tube, which includes a distal end having a circumferential wall that is shaped to define one or more perforations, into the body of the subject. The method further includes, subsequently to inserting the electrically-insulating tube, navigating the electrically-insulating tube through the body of the subject, until an outer electrode, which is disposed over the distal end of the electrically-insulating tube, lies at least partly within the thrombus. The method further includes, while the outer electrode lies at least partly within the thrombus, applying a positive voltage between the outer electrode and an inner electrode that is disposed, within the tube, opposite the perforations, such that electric current flows through the perforations, causing the thrombus to adhere to the outer electrode. The method further includes, while the thrombus adheres to the outer electrode, removing the thrombus from the body of the subject, by withdrawing the electrically-insulating tube.

In some embodiments, applying the positive voltage includes continuing to apply the positive voltage while withdrawing the electrically-insulating tube.

In some embodiments, the method further includes, while the outer electrode lies at least partly within the thrombus, applying suction to the thrombus via the perforations.

In some embodiments, the distal end of the electrically-insulating tube is shaped to define a distal opening, and the method further includes, prior to applying the suction, sealing the distal opening by inflating a balloon at the distal end of the electrically-insulating tube.

In some embodiments, the method further includes, subsequently to the thrombus adhering to the outer electrode, deflating the balloon, and withdrawing the electrically-insulating tube includes withdrawing the electrically-insulating tube while aspirating any detached portions of the thrombus through the distal opening.

In some embodiments,
   the distal end of the electrically-insulating tube is a first distal end,
   the inner electrode includes an electrically-conducting tube that includes a second distal end and is shaped to define a lumen,
   the balloon is coupled to the second distal end, and
   inflating the balloon includes inflating the balloon by passing a fluid through the lumen.

In some embodiments, inflating the balloon includes inflating the balloon such that the balloon protrudes from the distal end of the electrically-insulating tube.

In some embodiments,
   the distal end of the electrically-insulating tube is shaped to define a distal opening,
   the inner electrode includes a wire including an enlarged distal head, and
   the method further includes, prior to applying the suction, sealing the distal opening with the enlarged distal head.

In some embodiments, applying the suction includes continuing to apply the suction while withdrawing the electrically-insulating tube.

In some embodiments, the distal end is shaped to define a distal opening, and the method further includes, by applying the suction, aspirating any detached portions of the thrombus through the distal opening.

In some embodiments,
   at least some of the perforations are arranged in a row, a largest perforation in the row being larger than other perforations in the row,
   navigating the electrically-insulating tube through the body of the subject includes navigating the electrically-insulating tube through the body of the subject until the largest perforation is aligned with a proximal end of the thrombus, and
   applying the positive voltage includes applying the positive voltage while the largest perforation is aligned with the proximal end of the thrombus.

In some embodiments,
   the inner electrode includes a wire,
   the method further includes, prior to navigating the electrically-insulating tube through the body of the subject, passing the wire through the thrombus, and
   navigating the electrically-insulating tube through the body of the subject includes navigating the electrically-insulating tube over the wire.

In some embodiments, the method further includes, prior to applying the voltage, withdrawing the wire into the electrically-insulating tube.

In some embodiments, applying the positive voltage includes applying the positive voltage while a distal tip of the inner electrode is aligned with a distalmost one of the perforations.

There is further provided, in accordance with some embodiments of the present invention, a method for removing a thrombus from a body of a subject. The method includes inserting an electrically-insulating tube, which includes a distal end shaped to define a distal opening, into the body of the subject. The method further includes, subsequently to inserting the electrically-insulating tube, navigating the electrically-insulating tube through the body of the subject, until an outer electrode, which is disposed over the distal end of the electrically-insulating tube, lies at least partly within the thrombus. The method further includes, while the outer electrode lies at least partly within the thrombus, applying a positive voltage between the outer electrode and an inner electrode that is disposed at least partly within the distal end of the electrically-insulating tube, such that electric current flows between the outer electrode and the inner electrode, causing the thrombus to adhere to the outer electrode. The method further includes, while the thrombus adheres to the outer electrode, removing the thrombus from the body of the subject by withdrawing the electrically-insulating tube while aspirating any detached portions of the thrombus through the distal opening.

In some embodiments, applying the positive voltage includes continuing to apply the positive voltage while withdrawing the electrically-insulating tube.

In some embodiments,
the inner electrode includes a wire,
the method further includes, prior to navigating the electrically-insulating tube through the body of the subject, passing the wire through the thrombus, and
navigating the electrically-insulating tube through the body of the subject includes navigating the electrically-insulating tube over the wire.

In some embodiments, the method further includes, prior to applying the voltage, withdrawing the wire into the electrically-insulating tube.

The present invention will be more fully understood from the following detailed description of embodiments thereof, taken together with the drawings, in which:

BRIEF DESCRIPTION OF THE DRAWINGS

FIG. 2 is a longitudinal cross-section through part of an electrically-insulating tube, in accordance with some embodiments of the present invention;

FIGS. 7-8 are schematic illustrations of apparatuses for removal of a thrombus from a body of subject, in accordance with some embodiments of the present invention; and FIG. 9 is a schematic illustration of an inner electrode having an enlarged distal head, in accordance with some embodiments of the present invention.

DETAILED DESCRIPTION OF EMBODIMENTS

Overview

Figure 1A:
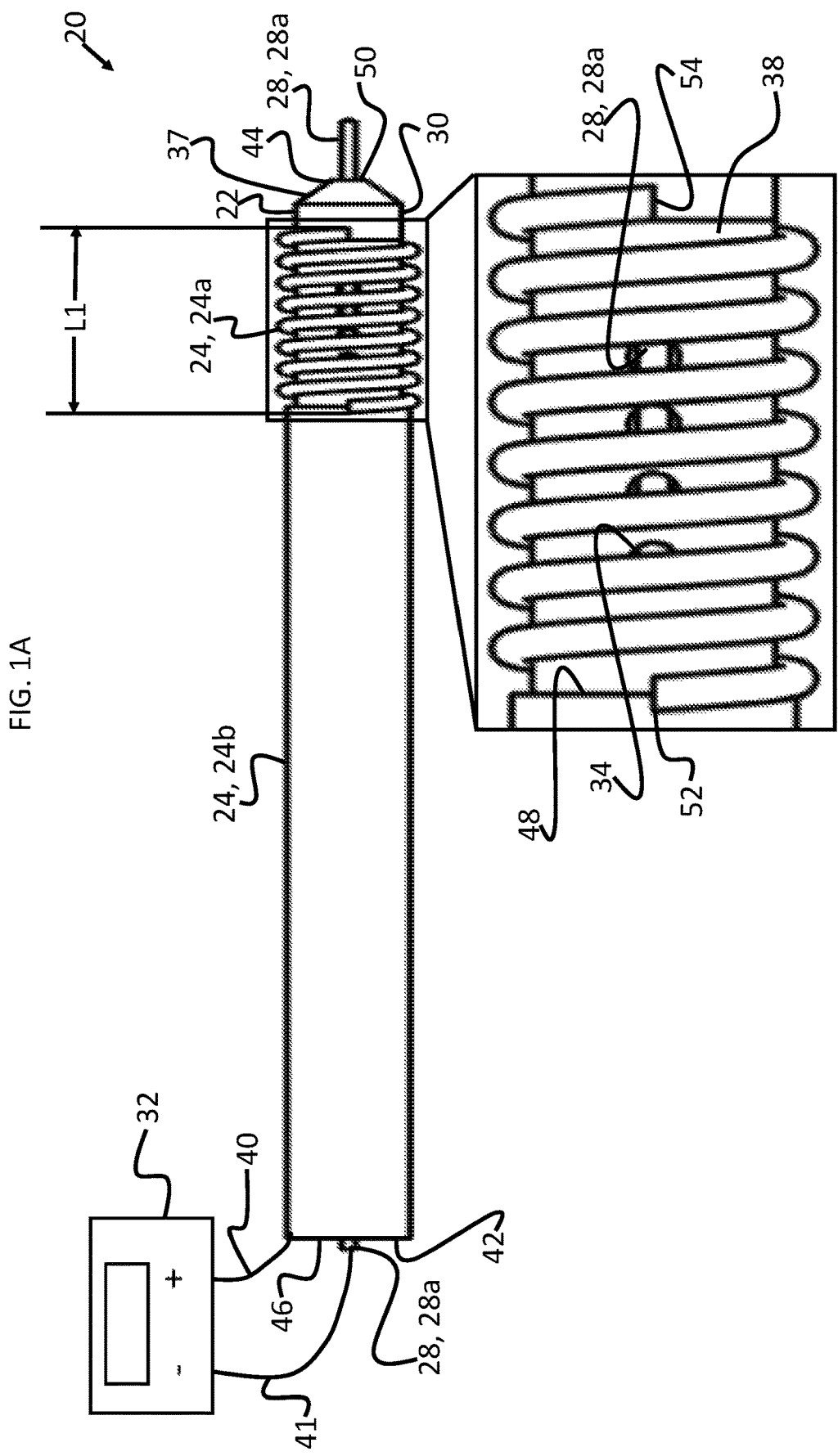
FIGS. 1A-B are schematic illustrations of an apparatus for removing a thrombus from a body of a subject, in accordance with some embodiments of the present invention.

Embodiments of the present invention include apparatuses and methods for a thrombectomy, i.e., for the removal of a thrombus from the body of a subject. In the context of the present application, including the claims, a "thrombus" may include any material that at least partly occludes a passageway, such as a blood vessel, within the subject's body. For example, a thrombus may include coagulated blood, fat, cholesterol, plaque, or any foreign material originating from outside the body.

In general, the thrombectomy techniques described herein involve applying a voltage between two electrodes that are radially separated from one another. For example, one thrombectomy device described herein comprises an outer electrode disposed over the distal end of an electrically-insulating tube, which in turn contains an inner electrode. The wall of the tube is shaped to define one or more perforations, which are disposed beneath the outer electrode. The device is advanced through the blood vessel, until the outer electrode is lodged (or "embedded") within the thrombus. Subsequently, a positive voltage is applied between the outer and inner electrodes, such that electric current flows between the electrodes via the perforations, causing the negatively-charged thrombus to adhere to the positively-charged outer electrode. While the thrombus adheres to the outer electrode, the device, along with the thrombus, is withdrawn from the subject.

Advantageously, due to the radial separation between the two electrodes, along with the perforations in the tube that allow for the flow of electric current therethrough, relatively little current flows through the blood vessel and the nearby tissue. In contrast, if the two electrodes were longitudinally (or "axially") separated from one another during the application of the voltage, or if the wall of the tube were not perforated, more current might need to flow through the blood vessel and the nearby tissue. Furthermore, since the outer electrode is disposed over the tube, the outer electrode may contact the thrombus over a relatively large surface area, facilitating the application of a relatively large attractive electrostatic force to the thrombus. In contrast, if the outer electrode were carried to the thrombus within the tube and then advanced from the tube into the thrombus, the outer electrode might need to have a smaller profile, such as to fit within the tube.

Another advantage of the perforations is that a suction force may be applied, via the perforations, to the thrombus, thus causing the thrombus to be more strongly attached to the thrombectomy device, and helping to keep the thrombus attached while the device is withdrawn. In some embodiments, the distal opening of the tube remains open while the suction force is applied, such that the suction force also aspirates any bubbles or debris that collect while the voltage is applied and/or while the device is withdrawn. Advantageously, since the outer electrode is disposed over the tube, the outer electrode does not block the distal opening of the tube, such that bubbles and debris may be more effectively aspirated through the distal opening. In other embodiments, the distal opening remains closed while the suction force is applied, such that the suction force is concentrated at the perforations. In yet other embodiments, the distal opening is closed before the suction force is applied, but is opened after the thrombus is attached to the device, so as to facilitate aspirating bubbles and debris while the device is withdrawn. For example, prior to the application of the suction force, a balloon at the distal end of the tube may be inflated, so as to seal the distal opening of the tube. Subsequently to the attachment of the thrombus to the device, the balloon may be deflated, so as to facilitate aspiration while the device is withdrawn.

In some cases, the location of the proximal end of the thrombus is known, but the exact length of the thrombus is unknown. In such cases, if the perforations were uniformly sized, the suction and electrostatic forces might be extensively applied over portions of the tube that are not situated within the thrombus. Hence, in some embodiments, the perforations are not uniformly sized. Rather, one of the perforations is larger than the other perforations, and this largest perforation is aligned with the proximal end of the thrombus. For example, the most proximal perforation may be larger than the more distal perforations, and this perforation may be aligned with the proximal end of the thrombus.

In other embodiments, the electrically-insulating tube is not perforated. In such embodiments, the applied suction force is concentrated at the distal opening of the tube, such as to provide better aspiration of any bubbles or debris generated during the procedure, relative to if the tube were perforated.

In some embodiments, the inner electrode comprises a wire that runs through the length of the tube. In such embodiments, the inner electrode may additionally function as a guidewire, to facilitate advancement of the tube through the vasculature of the subject. In other embodiments, the inner electrode comprises an inner, electrically-conducting tube having perforations that are aligned with those of the outer, electrically-insulating tube.

Apparatus Description

Figure 1B:
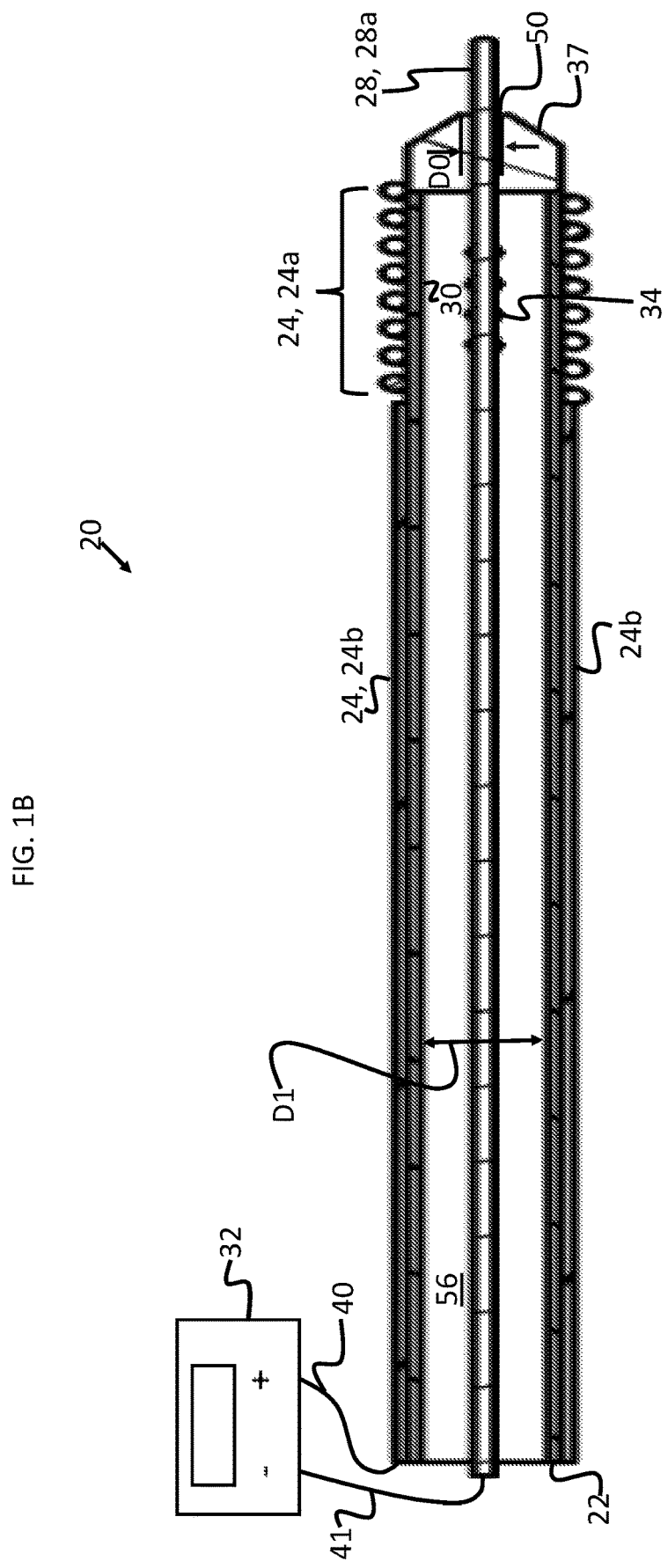

Reference is initially made to FIGS. 1A-B, which are schematic illustrations of an apparatus 20 for removing a thrombus from a body of a subject, in accordance with some embodiments of the present invention. (FIG. 1B shows a longitudinal cross-section through apparatus 20.)

Apparatus 20 comprises an electrically-insulating tube 22, which is configured for insertion into the body of a subject. Tube 22 may be made of any suitable biocompatible insulating material, such as silicone, polyurethane, polyethylene, or polytetrafluoroethylene. Tube 22 comprises a distal end 30 having a circumferential wall 38 that is shaped to define one or more perforations 34. (Hence, tube 22 may be referred to as a "perforated tube.") Tube 22 is shaped to define an inner lumen 56, which is surrounded by the circumferential wall of the tube.

Apparatus 20 further comprises an outer electrode 24, which is disposed over at least part of distal end 30, and an inner electrode 28, which is configured to lie within inner lumen 56. A first wire 40 connects outer electrode 24 to the positive terminal of a voltage source 32, which is disposed externally to the subject, while a second wire 41 connects inner electrode 28 to the negative terminal of the voltage source. As further described below with reference to FIG. 6, while outer electrode lies at least partly within the thrombus (typically, while in contact with the thrombus) and inner electrode 28 lies opposite perforations 34 (e.g., with the distal tip of the inner electrode being aligned with the distalmost perforation), voltage source 32 applies a positive voltage between outer electrode 24 and inner electrode 28. The positive voltage causes the outer electrode to attract the negatively-charged thrombus, such that the thrombus adheres to the outer electrode.

Typically, each of the electrodes is constructed of a highly conductive biocompatible metal. To increase the effectivity of the applied positive voltage, the outer electrode may have a higher electronegativity than that of the inner electrode. Thus, for example, the outer electrode may be made of gold, platinum, or any alloy thereof (such as an alloy of platinum and iridium), while the inner electrode may be made of stainless steel, Nitinol, or titanium.

In some embodiments, at least one of the electrodes is at least partly radiopaque, and/or comprises one or more radiopaque markers, to facilitate navigation under fluoroscopy. Similarly, distal end 30 may comprise one or more radiopaque markers, to facilitate navigation of tube 22 under fluoroscopy.

In some embodiments, as shown in FIG. 1A, outer electrode 24 comprises two portions: a distal portion 24a, which wraps around distal end 30 of the tube, and a proximal portion 24b. The distal end 48 of proximal portion 24b is connected to distal portion 24a and the proximal end 46 of proximal portion 24b is connected to first wire 40, such that distal portion 24a is connected to voltage source 32 via proximal portion 24b. Typically, the length L1 of distal portion 24a is between 5 and 150 mm, such as between 10 and 50 mm. The proximal end 52 of distal portion 24a is typically positioned proximally to the proximalmost perforation 34, while the distal end 54 of distal portion 24a is typically positioned distally to the distalmost perforation 34.

In some embodiments, the distal portion of the outer electrode comprises a coil, of a constant or variable pitch, that coils around distal end 30. Alternatively, the distal portion of outer electrode 24 may comprise an electrically-conductive braid or mesh that is wrapped around distal end 30. (In some cases, the distal portion of the outer electrode may partially cover perforations 34, as shown in FIG. 1A.) The proximal portion of the outer electrode may comprise an electrically-conducting tube that passes over tube 22, and/or an electrically-conducting braid, mesh, or coil that wraps around tube 22. The proximal portion of the outer electrode may be made of any suitable material, such as stainless steel, Nitinol, or titanium, and may be coated for improved lubricity.

In other embodiments, outer electrode 24 comprises a single electrically-conductive tube, mesh, braid, or coil that is proximally connected to first wire 40, and extends from the proximal end of tube 22 over at least some of distal end 30. For example, FIGS. 7-8, described below, show embodiments in which outer electrode 24 comprises a single coil. For embodiments in which the outer electrode comprises a tube, the tube may be shaped to define one or more perforations that are aligned with perforations 34.

Typically, the outer electrode is affixed to tube 22, such that the outer electrode does not slide along the tube. In some embodiments, however, the outer electrode may slide along tube 22.

In some embodiments, inner electrode 28 comprises a wire 28a. In such embodiments, wire 28a may facilitate guiding tube 22 to the thrombus, in addition to facilitating the aforementioned application of voltage. For example, wire 28a may be inserted into the subject, and then navigated, under fluoroscopic imaging or any other suitable imaging technique, to the thrombus. Next, wire 28a may be passed through the thrombus. Subsequently, tube 22 (and outer electrode 24) may be passed over the wire, until the outer electrode is disposed within the thrombus.

Alternatively, a separate guidewire may be used to guide tube 22 to the thrombus. After the outer electrode is lodged within the thrombus, the guidewire may be withdrawn, and wire 28a may then be passed through tube 22, to the distal end of the tube.

During the application of voltage between wire 28a and the outer electrode, the distal portion of the wire is positioned within the distal end of the tube, opposite (or "behind") the perforations, such that the electric current that flows between the electrodes may pass through the perforations. For example, the distal tip of the wire may be aligned with the distalmost perforation. In some embodiments, most of wire 28a is coated with an insulating material, with only the distal portion of the wire being uncoated.

The diameter D1 of inner lumen 56 of tube 22 is typically between 0.25 and 5 mm, such as between 0.4 and 2 mm Such a diameter is generally large enough to allow the passage of electrode 28, along with any aspirated debris, through tube 22, yet is small enough to facilitate navigation of the tube through the vasculature of the subject.

In some embodiments, distal end 30 is shaped to define a distal opening 50. In some such embodiments, distal opening 50 is sufficiently wide such that, while the voltage is applied between the electrodes, any detached portions of the thrombus may be aspirated through distal opening 50 by the suitable application of suction through tube 22. (In other words, the distal opening may function as an aspiration port.) For example, the diameter D0 of distal opening 50 may be approximately equal to diameter D1 of the tube lumen. In other such embodiments, D0 is significantly less than D1, such that the suction force applied through tube 22 is concentrated at perforations 34, thus facilitating better capture of the thrombus. For example, D0 may be approximately the same as that of wire 28a (or that of a typical guidewire), e.g., between 0.2 and 1 mm, with D1 being at least twice D0.

In other embodiments, distal end 30 is closed, i.e., distal end 30 is not shaped to define a distal opening, such that the applied suction force is fully concentrated at perforations 34. In such embodiments, apparatus 20 is advanced without the use of a guidewire. For example, apparatus 20 may be passed through a catheter. Alternatively, tube 22 may be shaped to define another lumen in addition to lumen 56, and rapid exchange techniques may be used to position the apparatus.

In some embodiments, distal end 30 tapers distally to the perforations, such that distal end 30 comprises a pointy distal tip configured to penetrate the thrombus. For example, the inner diameter of distal end 30 may decrease from D1 to D0, where D0 is less than 50% of D1, over a length of 1-3 mm. As shown in FIG. 1A, distal end 30 may taper distally by virtue of comprising a tapered end cap 37, which is fastened to the main body of tube 22.

It is noted that even in embodiments in which distal opening 50 is significantly narrowed or non-existent, the suction force that is applied may perform an aspirating function, in addition to facilitating the capture of the thrombus. For example, as further described below with reference to FIG. 5, the applied suction force may aspirate bubbles that form near the inner electrode while the voltage is applied, provided that these bubbles form within the tube.

It is noted that the various tubes, wires and other longitudinal elements described herein are typically flexible, so as to facilitate passage of these elements through the vasculature of the subject. Each of these elements may have any suitable length, so as to allow the removal of a thrombus from any blood vessel belonging to the subject. For example, the distance between the proximal tip 42 of tube 22 and the distal tip 44 of tube 22 (i.e., the distal tip of distal end 30) may be between 20 and 200 cm, e.g., between 90 and 200 cm, such that the tube may extend from the exterior of the subject to the thrombus. (In view of the above, it is noted that FIG. 1A is not drawn to scale, in that the distal portion of apparatus 20 is drawn disproportionately large.)

Reference is now made to FIG. 2, which is a longitudinal cross-section through part of tube 22, in accordance with some embodiments of the present invention.

In some embodiments, as shown in FIG. 2, the inner electrode comprises an electrically-conducting tube (or "shaft") 28b, instead of wire 28a. Typically, in such embodiments, a separate guidewire guides the delivery of apparatus 20 to the thrombus. (As in FIGS. 1A-B, tube 22 may comprise end cap 37.)

Typically, electrically-conducting tube 28b is affixed to the inner wall of the electrically-insulating tube. In such embodiments, tube 28b is typically shaped to define one or more perforations that are aligned with perforations 34 in tube 22. In other embodiments, electrically-conducting tube 28b is slidably disposed within electrically-insulating tube 22. As described above for wire 28a, most of tube 28b may be coated with an insulating material, with only the distal portion of tube 28b—which may be shaped to define the aforementioned perforations—being uncoated. Typically, the outer diameter of electrically-conducting tube 28b is approximately equal to inner diameter D1 of the tube, such that tube 28b adheres to, or slides along, the inner wall of tube 22.

In yet other embodiments, the inner electrode may comprise an electrically-conducting coil, braid, or mesh, which may be affixed to the inner wall of tube 22.

Figure 3A:
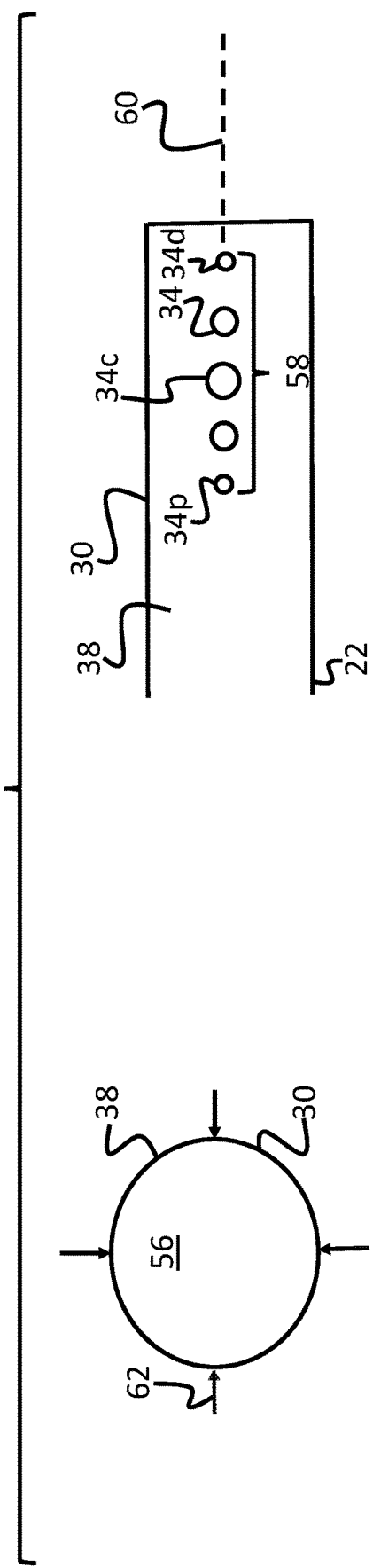
FIGS. 3A-B are schematic illustrations of the distal end of an electrically-insulating tube, in accordance with some embodiments of the present invention.
Figure 3B:
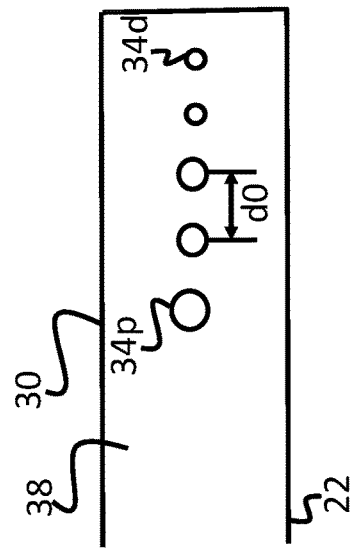

Reference is now made to FIGS. 3A-B, which are schematic illustrations of distal end 30 of electrically-insulating tube 22, in accordance with some embodiments of the present invention. (FIG. 3A shows both a frontal view of distal end 30, at the left of the figure, and a side view of distal end 30, at the right of the figure.)

Typically, perforations 34 are arranged in one or more rows 58, each of which may have any suitable orientation. For example, at least one row 58 may be oriented parallel to the longitudinal axis 60 of distal end 30, in a proximal-distal direction. Distal end 30 may be shaped to define any suitable number of rows, and each of the rows may include any suitable number of perforations, such as between one and ten perforations.

Typically, rows 58 are distributed circumferentially along circumferential wall 38. For example, distal end 30 may be shaped to define four rows of circumferentially-distributed perforations, such that a 90-degree angle separates each pair of successive rows. Such an example embodiment is illustrated in the frontal view of FIG. 3A, whereby a plurality of arrows 62 indicate the respective positions of four rows 58. (It is noted that the rows are not necessarily at the same longitudinal position, i.e., one of the rows may be situated more distally than another one of the rows.)

In some embodiments, for each of the rows, at least one of the perforations in the row is larger than the other perforations in the row. For example, as shown in FIG. 3A, at least one of the perforations between the proximalmost perforation 34p and the distalmost perforation 34d, such as a central perforation 34c, may be larger than each of the other perforations in the row. Furthermore, the size of the perforations may decrease from the middle of the row, such that proximalmost perforation 34p and distalmost perforation 34d are smaller than each of the other perforations in the row. Alternatively, as shown in FIG. 3B, proximalmost perforation 34p may be larger than the other perforations in the row. In addition, the size of the perforations may decrease from the proximal end of the row, such that distalmost perforation 34d is the smallest perforation in the row.

Typically, the size of each perforation is between $7.5 \times 10^{-5}$ and 10 mm$^2$. In some embodiments, for example, each perforation is circular, having a diameter of between 0.01 and 3.5 mm. For example, the largest perforation in each row may have a diameter of between 0.1 and 3.5 mm, with the smallest perforation have a diameter of between 0.01 and 0.3 mm. Alternatively or additionally, the combined size of the perforations in each row may be between 0.05 and 10 mm$^2$, and/or the combined size of all of the perforations, over all of the rows, may be between 0.2 and 20 mm$^2$. Alternatively or additionally, to prevent any pressure drops when suction is applied, this latter combined size may be larger than the circular cross-sectional area of lumen 56.

Typically, within any given row, each pair of successive perforations is separated by a distance d0 that is between 0.1 and 4 mm. In some embodiments, distance d0 varies across the row. For example, as shown in FIG. 3A, the distalmost perforation may be spaced from its proximally-neighboring perforation by a greater distance from that which separates the proximalmost perforation from its distally-neighboring perforation.

Figure 6:
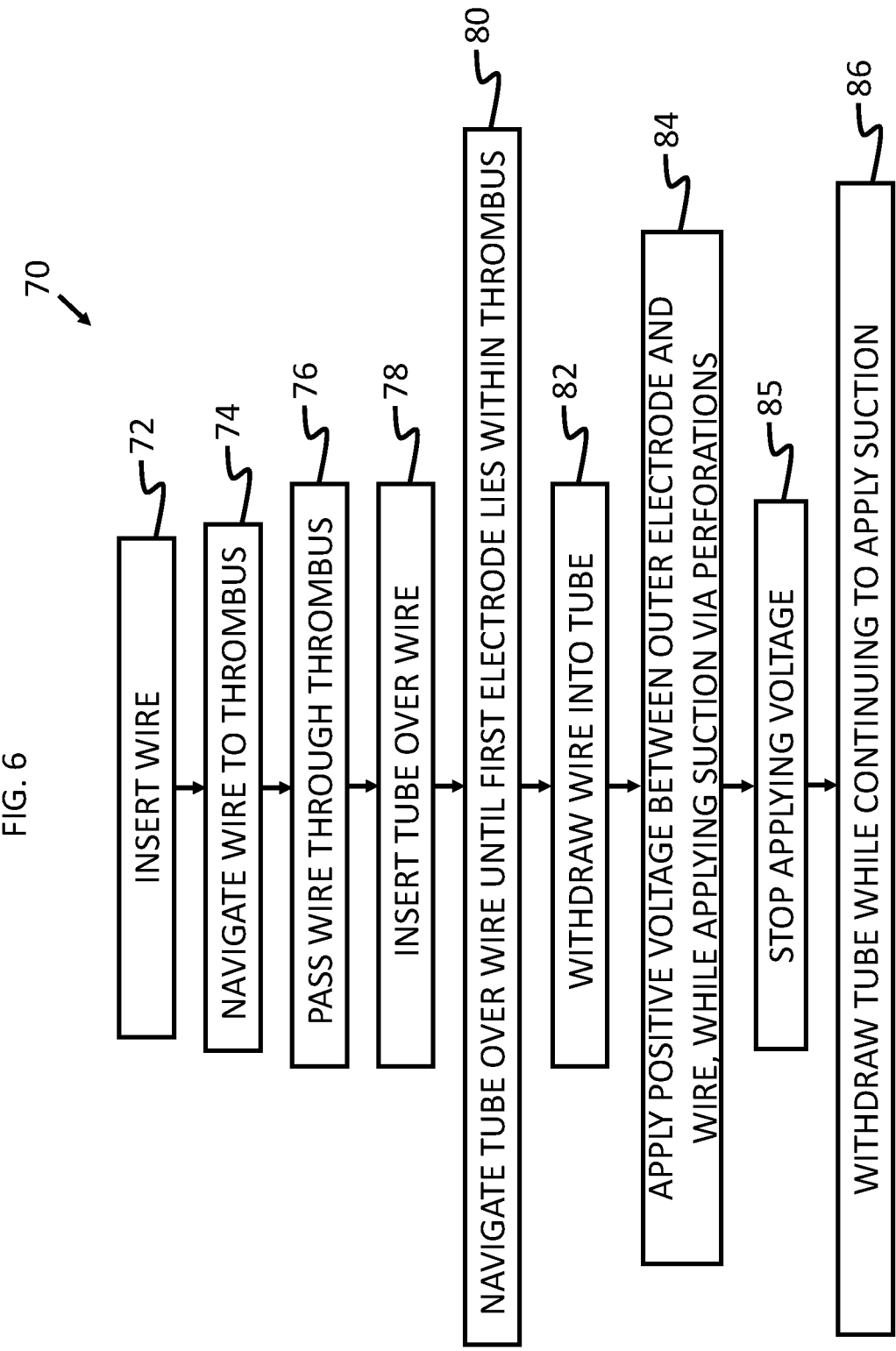
FIG. 6 is a flow diagram for a method for removing a thrombus from a body of a subject, in accordance with some embodiments of the present invention.

As further described below with reference to FIG. 6, while the outer electrode lies at least partly within the thrombus, suction is applied to the thrombus via the perforations. In general, the sizes of, and spacings between, the perforations may be matched to the location, size, and/or shape of the thrombus, to optimize the distribution of the electrostatic and suction forces applied to the thrombus. For example, as described above in the Overview, the largest perforations may be aligned with the proximal end of the thrombus.

Any suitable suction-applying device, such as a pump or syringe, may be used to apply the aforementioned suction force. Advantageously, provided that distal end 30 is open, the application of suction through tube 22 may further help aspirate bubbles and/or debris through distal opening 50.

In alternate embodiments, tube 22 is not perforated. Rather, apparatus 20 comprises a perforated insulating sheath that covers the distal end of the tube, the inner electrode being disposed between the outer wall of the tube and the insulating sheath, and the outer electrode being disposed over the insulating sheath. Typically, however, as described above, apparatus 20 does not comprise a perforated sheath covering the tube; rather, the tube itself is perforated.

Figure 4:
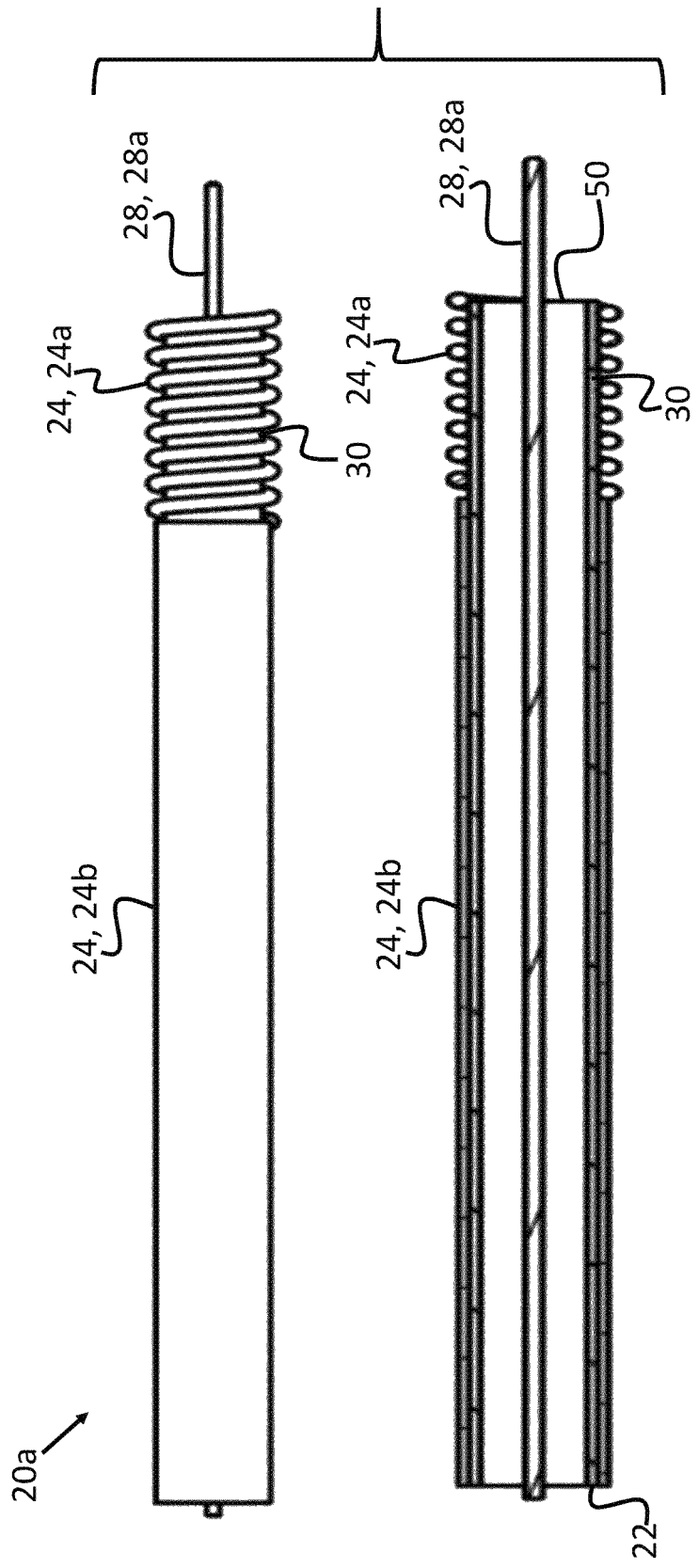
FIG. 4 is a schematic illustration of an apparatus for removing a thrombus from a body of a subject, in accordance with other embodiments of the present invention.

Reference is now made to FIG. 4, which is a schematic illustration of an apparatus 20*a* for removing a thrombus from a body of a subject, in accordance with other embodiments of the present invention. FIG. 4 includes both a side view of, and longitudinal cross-section through, apparatus 20*a*.

In several respects, the features of apparatus 20*a* are similar to those of apparatus 20. For example, in apparatus 20*a*, outer electrode 24 and inner electrode 28 are spaced radially from one another, with electrically-insulating tube 22 separating between the two electrodes. Similarly, each of the electrodes may have any of the forms described above, such that, for example, the outer electrode may comprise a coil, a mesh, a braid, and/or a tube, while the inner electrode may comprise a wire, a coil, a mesh, a braid, and/or a tube. Similarly, as in the case of apparatus 20, during the application of a voltage between the two electrodes, the inner electrode is positioned beneath the outer electrode, e.g., with the distal tip of the inner electrode being aligned with, or within several millimeters of, distal opening 50. Likewise, a pump or other suction-applying device may apply suction through tube 22 while the voltage is applied, and/or subsequently to the application of the voltage.

Apparatus 20*a* is different from apparatus 20, however, in that, in apparatus 20*a*, distal end 30 is not perforated. Due to the lack of perforations in distal end 30, electric current flows entirely through distal opening 50 while the voltage is applied between the electrodes. Advantageously, however, more suction force is concentrated at distal opening 50, such as to achieve better aspiration of any bubbles and debris that accumulate during the procedure.

Figure 5:
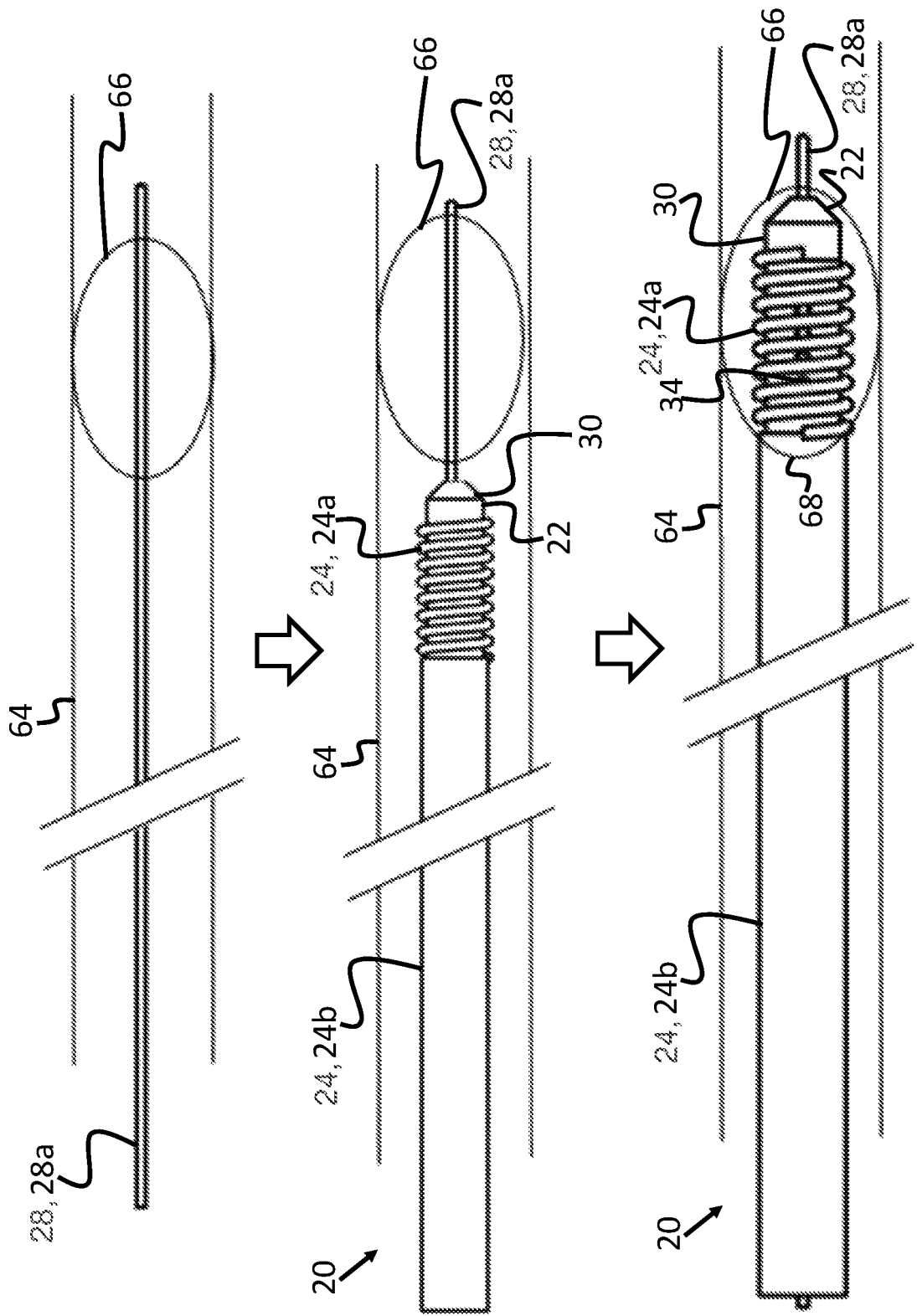
FIG. 5 is a schematic illustration showing the delivery of an apparatus to a thrombus, which is located within a blood vessel of a subject, in accordance with some embodiments of the present invention.

Reference is now made to FIG. 5, which is a schematic illustration showing the delivery of apparatus 20 to a thrombus 66, which is located within a blood vessel 64 of a subject, in accordance with some embodiments of the present invention.

First, as shown in the top portion of FIG. 5, wire 28*a* is navigated, under fluoroscopy or any other suitable imaging modality, through the vasculature of the subject, until the wire reaches blood vessel 64. Subsequently, wire 28*a* is passed through thrombus 66. Next, as shown in the middle portion of FIG. 5, perforated tube 22 is inserted into the vasculature of the subject, and is then navigated, through the vasculature, to blood vessel 64. (Perforations 34 are not shown in this portion of the figure.) Subsequently, tube 22 is navigated through the vasculature, until, as shown in the bottom portion of FIG. 5, outer electrode 24, which is disposed over distal end 30, lies at least partly within the thrombus. (As described above with reference to FIGS. 3A-B, in some embodiments, tube 22 may be navigated through the vasculature until the largest perforations are aligned with the proximal end 68 of the thrombus.)

Next, prior to applying voltage between the outer electrode and wire 28*a*, the wire may be withdrawn into tube 22, e.g., until the distal tip of the wire is aligned with the distalmost perforation(s). The withdrawal of the wire into the tube increases the proportion of the electric current that flows through the perforations while the voltage is applied. Furthermore, the withdrawal of the wire into the tube facilitates the aspiration of any bubbles that form near the wire, since most or all of these bubbles form within the tube.

The delivery of apparatus 20 to the thrombus, and the subsequent removal of the thrombus using apparatus 20, are hereby further described with reference to FIG. 6, which is a flow diagram for a method 70 for removing a thrombus from a body of a subject, in accordance with some embodiments of the present invention.

First, at a wire-inserting step 72, wire 28*a* is inserted into the subject. Subsequently, at a wire-navigating step 74, wire 28*a* is navigated to the thrombus. Next, at a thrombus-piercing step 76, wire 28*a* is passed through the thrombus, as described above with reference to the top portion of FIG. 5. Subsequently, at a tube-inserting step 78, tube 22 is inserted, over wire 28*a*, into the subject. Tube 22 is then navigated over the wire, at a tube-navigating step 80, until outer electrode 24 lies at least partly within the thrombus, as described above with reference to the middle and bottom portions of FIG. 5. Next, at a wire-withdrawing step 82, the wire is withdrawn into the tube, such that the distal end of the wire is disposed within the distal end of the tube, opposite the perforations.

Subsequently, at an applying step 84, voltage source 32 (FIG. 1) applies a positive voltage between the outer electrode and the wire, while a pump, or other suitable suction-applying device, applies suction to the thrombus via the perforations in the tube. The applied voltage causes electric current to flow through the perforations, such that the outer electrode attracts the thrombus. The applied suction supplements the applied voltage by pulling the thrombus radially inward, toward the tube, and may further aspirate any detached portions of the thrombus through the distal opening of the tube while the voltage is applied. In some embodiments, the application of suction begins before the application of voltage.

Typically, the voltage is applied for a duration that is sufficient for the thrombus to adhere to the outer electrode, without exposing the subject to any unnecessary risk. For example, this duration may be between one second and 10 minutes, such as between 5 seconds and 5 minutes, e.g., between 10 seconds and 2 minutes. Following this duration, the application of the voltage is stopped, at a voltage-stopping step 85. Finally, at a tube-withdrawing step 86, while the thrombus adheres to the outer electrode, the thrombus is removed from the body of the subject, by withdrawing the tube, over the wire, from the subject. (In some embodiments, the wire is withdrawn along with the tube, while in other embodiments, the wire is withdrawn only after the tube has been withdrawn.) While the tube is withdrawn, the application of suction continues, such as to help keep the thrombus attached to the outer electrode, and/or aspirate any detached portions of the thrombus through the distal end of the tube.

In alternate embodiments, the application of the voltage may continue during at least part of the time during which the tube is withdrawn.

As noted above, in some embodiments, the inner electrode does not comprise wire 28*a*, or wire 28*a* does not function as a guidewire. In such embodiments, a separate guidewire, instead of wire 28*a*, is inserted into the subject at wire-inserting step 72. Method 70 then proceeds as outlined above, until the completion of tube-navigating step 80. Following tube-navigating step 80, the guidewire is withdrawn from the body, and the inner electrode is then inserted into tube 22, until the distal end of the inner electrode is aligned with the distal perforations in the tube. Subsequently, applying step 84, along with the subsequent steps, are performed, as outlined above.

It is noted that the technique described above with reference to FIG. 6 may be used with apparatus 20*a* (FIG. 4), mutatis mutandis. For example, further to positioning the apparatus as described above, a suction force may be applied together with the positive voltage, and/or prior to or following the application of the voltage. Although this suction force does not draw the thrombus radially inward (due to the lack of perforations in the tube), this suction force may nonetheless aspirate any detached portions of the thrombus through the distal opening of the tube.

In general, the positive voltage signal that is applied between the electrodes may have any suitable form, such as any of the forms described in US Patent Application Publication 2011/0301594, whose disclosure is incorporated herein by reference. For example, the voltage signal may be a periodic signal that includes a sequence of pulses, each of these pulses, for example, being shaped as the positive half-wave of a sinusoidal signal, or having a trapezoidal shape. Alternatively, the voltage signal may be a direct current (DC) voltage signal. Typically, the voltage signal is unipolar. Although the amplitude of the voltage may have any suitable value, this amplitude is typically between 0.1 and 100 V, e.g., between 1 and 100 V, such as between 1 and 50 V, or between 4 and 40 V. Such an amplitude is large enough to be effective, yet small enough such as to avoid damaging the tissue near the thrombus.

For example, as described in US Patent Application Publication 2011/0301594 with reference to FIG. 1D thereof, each trapezoidal pulse of the applied voltage signal may (i) linearly ramp up from ground level (0 volts) to an amplitude of around 40 volts, over a time period of around 5 milliseconds, (ii) remain constant over a time period of around 5 milliseconds, and then (iii) linearly ramp down to ground level over a time period of around 5 milliseconds. Before the beginning of the subsequent pulse, the voltage may remain at ground level for another time period of around 5 milliseconds. In general, the applied voltage signal, if pulsatile, may have any suitable frequency, such as between 0.1 Hz to 100 MHz, e.g., around 50 Hz, as in the example immediately above. Typically, the voltage is applied such that a current having an amplitude of between 0.1 and 4 mA (e.g., 1-3 mA) is passed between the two electrodes.

In some embodiments, voltage source 32 is current-regulated, e.g., to between 0.1 and 4 mA, such as 1-3 mA. In other embodiments, the voltage source is voltage-regulated, e.g., to between 0.1 and 100 V, or any of the smaller subranges outlined above.

In alternate embodiments, when using apparatus 20*a*, a negative voltage, which dissolves the thrombus, is applied between the outer and inner electrodes, by connecting the outer electrode to the negative terminal of voltage source 32, and connecting the inner electrode to the positive terminal. As the negative voltage is applied, the dissolved pieces of thrombus material are aspirated though the distal opening of tube 22.

Reference is now made to FIG. 7, which is a schematic illustration of an apparatus 20*b* for removal of a thrombus from a body of subject, in accordance with some embodiments of the present invention.

Similarly to apparatus 20, in apparatus 20*b*, the distal end of tube 22 is open. However, apparatus 20*b* differs from apparatus 20 by virtue of comprising an inflatable balloon 90. Prior to applying the suction force through tube 22, balloon 90 is inflated at the distal end of tube 22, such that the balloon seals the distal end of the tube. The suction force is thus concentrated at perforations 34, such that the thrombus may be more effectively captured by the apparatus. Subsequently to capturing the thrombus, as the apparatus is withdrawn, the balloon may be deflated, so as to facilitate aspirating bubbles and debris through the distal end of the tube.

In some embodiments, inner electrode 28 comprises an electrically-conducting (typically metallic) tube 28*b*, shaped to define a lumen 88. In such embodiments, balloon 90 is coupled to the distal end of tube 28*b*, such that the interior of the balloon is in fluid communication with lumen 88. The proximal end of tube 28*b* is coupled to a syringe or other inflating device, such that the balloon may be inflated by passing a fluid (e.g., saline) through lumen 88. In other embodiments, inner electrode 28 comprises wire 28*a*, and a separate inflation tube, running alongside wire 28*a*, is connected to balloon 90. In such embodiments, the balloon may be coupled to the wire, alternatively or additionally to the inflation tube.

Advantageously, the balloon may act as a centering mechanism for the inner electrode, in addition to sealing tube 22. In other words, the balloon, when inflated, may position the inner electrode at the center of lumen 56.

Reference is now made to FIG. 8, which is a schematic illustration of apparatus 20*b*, in accordance with other embodiments of the present invention.

In FIG. 8, as in FIG. 2, the inner electrode comprises electrically-conducting tube 28*b*, which is disposed within tube 22 (typically flush with the inner wall of tube 22), and which is shaped to define perforations 35 that are aligned with perforations 34 in tube 22. Balloon 90 is coupled to the inner wall of tube 28*b*, at the distal end of tube 28*b*. An inflation tube (not shown), which runs, for example, along the inner wall of, or through the lumen of, tube 28b, connects the balloon to an inflating device at the proximal end of tube 22.

In general, for the embodiments of FIGS. 7-8, balloon 90 may have any suitable shape, such as a torus shape or ellipsoid shape. The balloon, at least when inflated, may protrude from the distal end of tube 22 (as shown in FIG. 8), such that the balloon may cushion the internal tissue of the subject from any impact with apparatus 20b.

In yet other embodiments, the balloon is coupled to the inner wall of tube 22, at the distal end of the tube.

Reference is now made to FIG. 9, which is a schematic illustration of an inner electrode having an enlarged distal head, in accordance with some embodiments of the present invention.

In some embodiments, wire 28a comprises an enlarged distal head 92 having a maximum diameter that is approximately equal to the inner diameter of tube 22. Distal head 92 generally serves the function of balloon 90, by sealing the distal end of tube 22 such as to concentrate the suction force at perforations 34. Distal head 92 may have any suitable shape, provided that—as noted above—at least some portion of the distal head is wide enough to seal the tube.

More particularly, tube 22 is first advanced over a guidewire to the thrombus. Next, the guidewire is withdrawn, and wire 28a is advanced through the tube to the distal end of the tube, such that the distal opening of tube becomes sealed. Alternatively, instead of using a separate guidewire, the tube may be advanced over wire 28a, until the distal end of the tube reaches the distal head of the wire. Subsequently, the suction force is applied.

Typically, following the capture of the thrombus, the wire is withdrawn together with the tube, so as to maintain the radial electrostatic force on the thrombus. Thus, the tube remains sealed by the wire, such that aspiration through the tube is inhibited. Nevertheless, the embodiment of FIG. 9 offers an advantage over that of FIGS. 7-8, in that the apparatus comprises fewer components, and is hence easier to manufacture.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus for removal of a thrombus from a body of a subject, the apparatus comprising:
   an electrically-insulating tube, which comprises a distal end having a circumferential wall that is shaped to define multiple perforations along a length of the distal end, configured for insertion into the body of the subject;
   an outer electrode wrapped around the distal end of the electrically-insulating tube from a first location proximal to a proximalmost one of the multiple perforations to a second location distal to a distalmost one of the multiple perforations, and configured to lie at least partly within the thrombus while the electrically-insulating tube is inside the body of the subject; and
   an inner electrode, configured to lie, within the electrically-insulating tube, opposite the multiple perforations such that the inner electrode is radially separated from the outer electrode, while the outer electrode lies at least partly within the thrombus,
   the outer electrode being configured to attract the thrombus while the outer electrode lies at least partly within the thrombus and the inner electrode lies opposite the multiple perforations when a positive voltage is applied between the outer electrode and the inner electrode such that an electric current flows through the multiple perforations.

2. The apparatus according to claim 1, wherein the distal end of the electrically-insulating tube is shaped to define a distal opening.

3. The apparatus according to claim 2, further comprising an inflatable balloon, configured to seal the distal opening when inflated at the distal end of the electrically-insulating tube.

4. The apparatus according to claim 3,
   wherein the distal end of the electrically-insulating tube is a first distal end,
   wherein the inner electrode comprises an electrically-conducting tube comprising a second distal end, and
   wherein the inflatable balloon is coupled to the second distal end.

5. The apparatus according to claim 3, wherein the inflatable balloon is coupled to an inner wall of the electrically-insulating tube at the distal end of the electrically-insulating tube.

6. The apparatus according to claim 2, wherein the inner electrode comprises a wire comprising an enlarged distal head configured to seal the distal opening.

7. The apparatus according to claim 1, wherein the distal end of the electrically-insulating tube is closed.

8. The apparatus according to claim 1, wherein the outer electrode comprises a coil that wraps around the distal end of the electrically-insulating tube.

9. The apparatus according to claim 8, wherein the coil wraps around the distal end of the electrically-insulating tube between the multiple perforations.

10. The apparatus according to claim 1, wherein the inner electrode comprises a wire.

11. The apparatus according to claim 1, wherein the inner electrode comprises an electrically-conducting tube.

12. A method for removing a thrombus from a body of a subject, the method comprising:
   inserting an electrically-insulating tube, which includes a distal end having a circumferential wall that is shaped to define multiple perforations along a length of the distal end, into the body of the subject;
   subsequently to inserting the electrically-insulating tube, navigating the electrically-insulating tube through the body of the subject, until an outer electrode, which is wrapped around the distal end of the electrically-insulating tube from a first location proximal to a proximalmost one of the multiple perforations to a second location distal to a distalmost one of the multiple perforations, lies at least partly within the thrombus;
   while the outer electrode lies at least partly within the thrombus, applying a positive voltage between the outer electrode and an inner electrode that is disposed, within the electrically-insulating tube, opposite the multiple perforations such that the inner electrode is radially separated from the outer electrode, such that an electric current flows through the multiple perforations, causing the thrombus to adhere to the outer electrode; and while the thrombus adheres to the outer electrode, removing the thrombus from the body of the subject, by withdrawing the electrically-insulating tube.

13. The method according to claim 12, further comprising, while the outer electrode lies at least partly within the thrombus, applying suction to the thrombus via the multiple perforations.

14. The method according to claim 13, wherein the distal end of the electrically-insulating tube is shaped to define a distal opening, and wherein the method further comprises, prior to applying the suction, sealing the distal opening by inflating a balloon at the distal end of the electrically-insulating tube.

15. The method according to claim 14, further comprising, subsequently to the thrombus adhering to the outer electrode, deflating the balloon, wherein withdrawing the electrically-insulating tube comprises withdrawing the electrically-insulating tube while aspirating any detached portions of the thrombus through the distal opening.

16. The method according to claim 14,
wherein the distal end of the electrically-insulating tube is a first distal end,
wherein the inner electrode includes an electrically-conducting tube that includes a second distal end and is shaped to define a lumen,
wherein the balloon is coupled to the second distal end, and
wherein inflating the balloon comprises inflating the balloon by passing a fluid through the lumen.

17. The method according to claim 14, wherein inflating the balloon comprises inflating the balloon such that the balloon protrudes from the distal end of the electrically-insulating tube.

18. The method according to claim 13,
wherein the distal end of the electrically-insulating tube is shaped to define a distal opening,
wherein the inner electrode includes a wire including an enlarged distal head, and
wherein the method further comprises, prior to applying the suction, sealing the distal opening with the enlarged distal head.

19. The method according to claim 13, wherein applying the suction comprises continuing to apply the suction while withdrawing the electrically-insulating tube.

20. The method according to claim 13, wherein the distal end is shaped to define a distal opening, and wherein the method further comprises, by applying the suction, aspirating any detached portions of the thrombus through the distal opening.

21. The method according to claim 12,
wherein the inner electrode includes a wire,
wherein the method further comprises, prior to navigating the electrically-insulating tube through the body of the subject, passing the wire through the thrombus, and
wherein navigating the electrically-insulating tube through the body of the subject comprises navigating the electrically-insulating tube over the wire.

* * * * *